US00PP11205P

United States Patent [19]

Bradford et al.

[11] Patent Number: Plant 11,205

[45] Date of Patent: Feb. 8, 2000

[54] PEACH TREE 'IVORY PRINCESS'

[76] Inventors: Lowell Glen Bradford, 12439 E. Savana Rd.; Norman G. Bradford, 11875 E. Savana Rd., both of Le Grand, Calif. 95333

[21] Appl. No.: 09/004,302

[22] Filed: Jan. 8, 1998

[51] Int. Cl.[7] ..... A01H 5/00

[52] U.S. Cl. ..... Plt./195

[58] Field of Search ..... Plt./195

[56] References Cited

U.S. PATENT DOCUMENTS

| | | | |
|---|---|---|---|
| P.P. 7,070 | 12/1989 | Bradford et al. | Plt./197 |
| P.P. 9,360 | 11/1995 | Bradford et al. | Plt./188 |
| P.P. 9,882 | 5/1997 | Zaiger et al. | Plt./195 |
| P.P. 10,190 | 1/1998 | Zaiger et al. | Plt./195 |

*Primary Examiner*—Howard J. Locker
*Assistant Examiner*—Wendy A Baker

[57] ABSTRACT

The present invention relates to a peach tree, *Prunus persica*, and more particularly to a new and distinct variety broadly characterized by a medium sized, vigorous, hardy, self-fertile, productive and regular bearing tree. The fruit matures under the ecological conditions described approximately the first week in June, with first picking on Jun. 1st, 1997. The fruit is uniformly medium in size, very good in flavor, attractively globose in shape, clingstone in type, firm in texture, white in flesh color, and mostly red in skin color. The variety was developed as a first generation cross using 'Crown Princess' (U.S. Plant Pat. No. 7,070) yellow flesh peach as the selected seed parent and 'June Pearl' (U.S. Plant Pat. No. 9,360) white flesh nectarine as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of peach tree, which has been denominated varietally as 'Ivory Princess'. The present variety was hybridized by us in 1992, grown as a seedling on its own roots in our greenhouse, and transplanted to a cultivated area of our experimental orchard at Bradford Farms near Le Grand, Calif. in Merced County (San Joaquin Valley). It was developed as a first generation cross using 'Crown Princess' (U.S. Plant Pat. No. 7,070) yellow flesh peach as the selected seed parent and 'June Pearl' (U.S. Plant Pat. No. 9,360) white flesh nectarine as the selected pollen parent. Subsequent to origination of the present variety of peach tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The fruit produced by the present variety exhibits the desirable characteristics common to its pollen parent, 'June Pearl' (U.S. Plant Pat. No. 9,360) white flesh nectarine, by producing clingstone fruit that is white in flesh color, subacidic and sweet in flavor, firm in texture, and mostly red in skin color, but is distinguished therefrom and an improvement thereon by producing fruit that is larger in size, rounder in shape, peach instead of nectarine, and that ripens about seven days earlier.

The present variety is similar to its selected seed parent, 'Crown Princess' (U.S. Plant Pat. 7,070) yellow flesh peach, by producing clingstone peaches that are globose in shape, nearly full red in skin color, and mature in early June, but is distinguished therefrom and an improvement thereon by producing fruit that is subacidic instead of acidic in flavor and that is white instead of yellow in flesh color.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 5, 1997. All major color code designations are by reference to the Inter-Society Color Council, Nation Bureau of Standards. Common color names are also used occasionally.

TREE

Size: Medium, surpassing a height of 10' [3.05 meters] and a spread of 7.5' [2.29 meters] during the 3rd growing season after typical dormant pruning each year.

Vigor: Vigorous, responding typically to irrigation and fertilization. The variety grows about 3' [0.91 meters] of surplus top-growth during the spring and summer.

Growth: Upright and dense.

Form: Vase formed.

Hardiness: Hardy with respect to central California winters.

Production: Productive, thinning necessary.

Bearing: Regular bearer with no alternate bearing yet observed.

Fertility: Self-fertile.

Trunk:

*Size.*—Medium, reaching a diameter of 3.5" [88.9 mm.] after the third growing season.

*Texture.*—Rough.

*Bark color.*—Grayish brown [61. gy.Br].

*Lenticels.*—Numerous. Color: Strong brown [55. s.Br]. Size: ⅛" to ⅜" [3.2–9.5 mm.].

Branches:
*Size.*—Medium, typical of *Prunus persica.*
*Texture.*—Smooth on 1st year wood, increasing roughness with age.
*Color.*—1st year wood topside: Grayish pink [8. gy.Pk]. 1st year wood underside: Brilliant yellow green [116. brill.YG]. Older wood: Moderate brown [58. m.Br].
*Lenticels.*—Numerous. Color: Strong brown [55. s.Br.]. Average Size: 1/16" [1.6 mm.].

Leaves:
*Size.*—Medium. Average length: 5½" [139.7 mm.]. Average width: 1½" [38.1 mm.].
*Thickness.*—Medium.
*Form.*—Elliptical.
*Apex.*—Acuminate.
*Base.*—Acute.
*Surface.*—Smooth.
*Color.*—Dorsal surface: Moderate olive green [125. mOlG]. Ventral surface: Moderate yellow green [120. m.YG].
*Margin.*—Finely serrate.
*Venation.*—Pinnately net veined.
*Petiole.*—Average Length: ⅜" [9.5 mm.]. Average Thickness: 1/16" [1.6 mm.]. Color: Moderate yellow green [120. m.YG].
*Stipules.*—*Numerous,* 2 per leaf, up to 6 per growing tip. Average Length: ⅜" [9.5 mm.].
*Glands.* —Numbers: 2–4 per leaf. Position: Most alternately but a few oppositely positioned on the petiole and the base of blade. Size: Small. Form: Reniform. Color: Moderate yellow green [120. m.YG].

Flower buds:
*Hardiness.*—Hardy, with respect to central California winters.
*Diameter.*—Typically ⅜" [9.5 mm.] 1 week before bloom.
*Length.*—Typically ¾" [19.1 mm.] 1 week before bloom.
*Form.*—Free.
*Surface.*—Pubescent.
*Color.*—Moderate purplish pink [250. m.pPk].

Flowers: Perfect, complete, perigynous, usually a single pistil, typically thirty or more stamens, five sepals and petal locations alternately positioned.
*Type.*—Showy.
*Number of petals.*—Usually five, many doubles.
*Petal shape.*—Circular.
*Petal margin.*—Slightly wavy.
*Average petal diameter.*—13/16" [20.6 mm.].
*Petal color.*—Pale purplish pink [252. p.pPk].
*Anther color.*—Dark red [16. d.Red].
*Average pistil length.*—⅝" [15.9 mm.].
*Fragrance.*—Strong when nectar is present.
*Average flower diameter.*—2" [50.8 mm.].
*Blooming period.*—Late as compared with other varieties.
*Onset of bloom.*—One percent on Mar. 7, 1997.

FRUIT

Maturity when described: Firm ripe, Jun. 5, 1997.
Date of first picking: Jun. 1, 1997.
Date of last picking: Jun. 10, 1997.
Size: Uniform, medium.
*Average diameter axially.*—2⅝" [66.7 mm].
*Average diameter across suture plane.*—2⅝" [66.7 mm].
*Typical weight.*—6.07 ounces [172 grams].
Form: Uniform, symmetrical, globose.
*Longitudinal section form.*—Round.
*Transverse section through diameter.*—Round.
Suture: A sharp crease in the stem cavity transforming to an inconspicuous shallow line extending past the apex, having a slight depression beyond the pistil point.
Ventral surface: Strongly rounded, slightly lipped throughout.
Lips: Slightly unequal.
Cavity: Flaring, elongated in the suture plane, suture showing on one side, stem markings typical.
Base: Rounded to truncate.
Apex: Rounded.
Pistil point: Very short, apical, usually depressed within the suture.
Stem: Medium.
*Average length.*—⅜" [9.5 mm.].
*Average width.*—3/16" [4.8 mm.].

Skin:
*Thickness.*—Medium.
*Texture.*—Medium.
*Tenacity.*—Tenacious to flesh.
*Astringency.*—Slight to none.
*Tendency to crack.*—None observed.
*Color.*—Very dark red [17. v.d.R] blending into a dark pink [6. d.Pk] background, with pale greenish yellow [104. p.gY] stem markings typical on the base.

Down: Scant, short, does not roll up when rubbed.

Flesh:
*Color.*—Yellowish white [92. yWhite], with a very minor amount of strong pink [2. s.Pk] streaking toward the skin on the more mature fruits.
*Amygdalin.*—Scarce.
*Juice.*—Abundant, rich.
*Texture.*—Firm, crisp.
*Fibers.*—Abundant, fine, tender.
*Ripens.*—Evenly.
*Flavor.*—Subacidic and sweet with 14 to 16 brix.
*Aroma.*—Slight.
*Eating quality.*—Very good.

STONE

Type: Clingstone.
Form: Oval.
Base: Straight.
Apex: Acute to acuminate.
Sides: Equal.
Surface: Regularly furrowed near the apex and pitted toward the base.
Ridges: Jagged toward the base.
Color: Light yellowish brown [76. l.yBr].
Pit wall: 5/16" [7.9 mm.] thick.
Tendency to split: None observed.

Kernel:
*Form.*—Oval.
*Color.*—Pale yellow [89. p.Y] with deep yellowish brown [75. deep yBr] veins when first exposed.
*Taste.*—Bitter.
*Viable.*—Yes.
*Average width.*—7/16" [11.1 mm.].
*Average length.*—⅝" [15.9 mm.].

Pellicle color: Dark yellowish brown [78. d.yBr].
Amygdalin: Abundant.

USE

Market: Fresh and long distance shipping.
Keeping quality: Fruit quality observed to remain in good condition in excess of 17 days in standard cold room at 36° Fahrenheit [2° Celsius].
Resistance to insects: No unusual susceptibilities noted.
Resistance to diseases: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, which produces fruit that exhibits the desirable characteristics common to its pollen parent, 'June Pearl' (U.S. Plant Pat. No. 9,360) white flesh nectarine, by producing clingstone fruit that is white in flesh color, subacidic and sweet in flavor, firm in texture, and mostly red in skin color, but is distinguished therefrom and an improvement thereon by producing fruit that is larger in size, rounder in shape, peach instead of nectarine, and that ripens about seven days earlier.

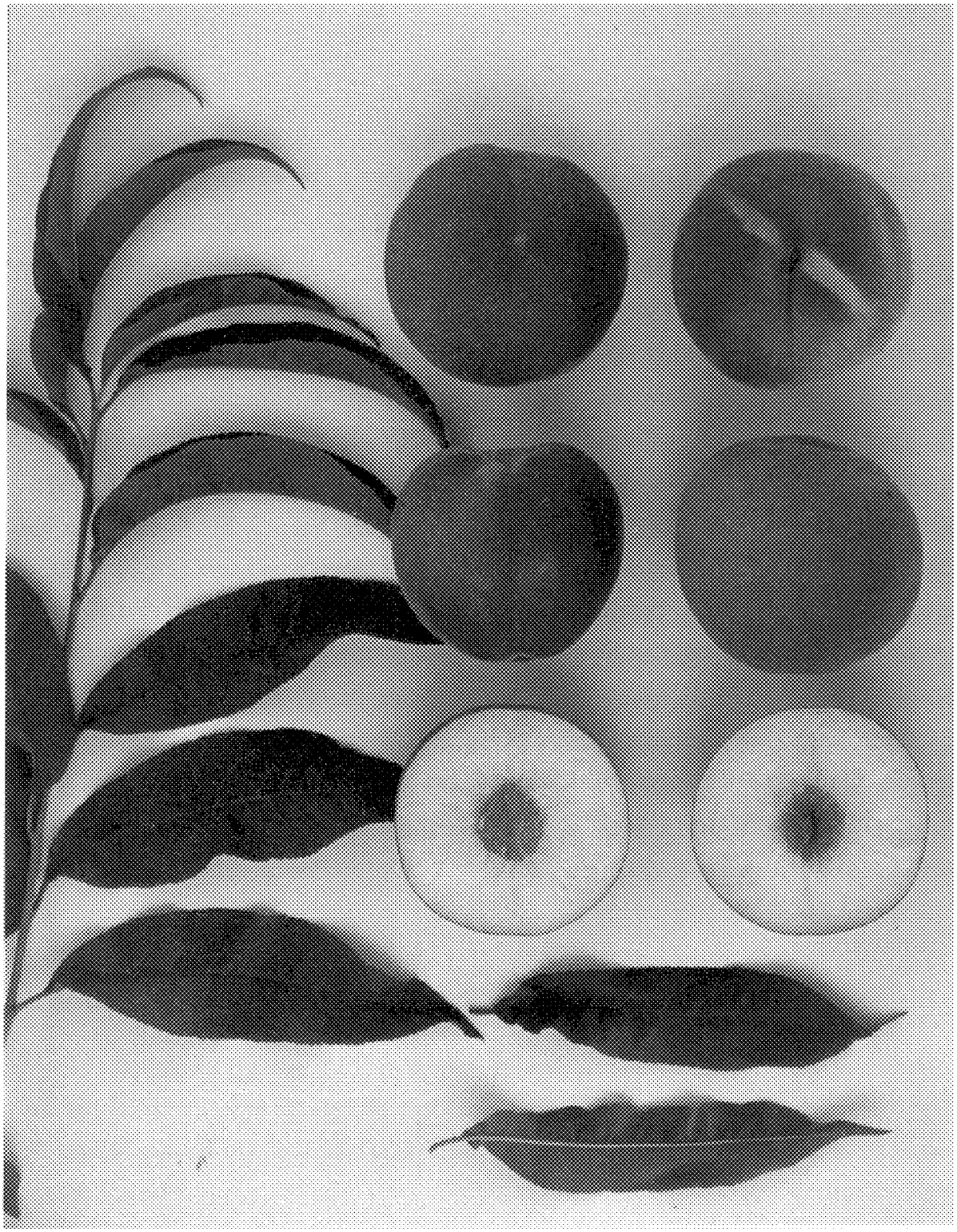

* * * * *